United States Patent
Genin

(10) Patent No.: US 8,801,588 B2
(45) Date of Patent: Aug. 12, 2014

(54) DEVICE FOR SELECTING A BEAM TRIGGERING APPARATUS

(75) Inventor: Frédéric Genin, Ottignies-Louvain-la-Neuve (BE)

(73) Assignee: Ion Beam Applications S.A., Louvain-la-Neuve (*) Notice: Subject to any disclaimer, the term of this patent is extended or adjusted under 35 U.S.C. 154(b) by 871 days.

(21) Appl. No.: 12/937,951

(22) PCT Filed: Apr. 16, 2009

(86) PCT No.: PCT/EP2009/054529
§ 371 (c)(1),
(2), (4) Date: Dec. 8, 2010

(87) PCT Pub. No.: WO2009/127689
PCT Pub. Date: Oct. 22, 2009

(65) Prior Publication Data
US 2011/0092760 A1    Apr. 21, 2011

(30) Foreign Application Priority Data

Apr. 16, 2008 (EP) .................................. 08154632

(51) Int. Cl.
*G21K 5/00* (2006.01)

(52) U.S. Cl.
USPC ............................................................ 600/1

(58) Field of Classification Search
USPC .......................... 600/1–9; 250/492.1–492.3; 378/145–161
See application file for complete search history.

(56) References Cited

U.S. PATENT DOCUMENTS

| 4,991,587 A | 2/1991 | Blakeley et al. |
| 6,725,078 B2* | 4/2004 | Bucholz et al. ............... 600/410 |

FOREIGN PATENT DOCUMENTS

| WO | 98/16151 A1 | 4/1998 |
| WO | 99/42034 A2 | 8/1999 |

* cited by examiner

*Primary Examiner* — Samuel Gilbert
(74) *Attorney, Agent, or Firm* — Fitch, Even, Tabin & Flannery LLP

(57) ABSTRACT

The present invention is related to device for selecting one of several triggering apparatuses, which are simultaneously connectable to said device. The triggering apparatuses are arranged for producing each a triggering signal to enable/disable one or more components of a radiation treatment apparatus. The triggering signals depend on detected parameters. The device is configured to receive triggering signals from the several triggering apparatuses, when all of the apparatuses are connected to the device, to receive a selection of one of the triggering apparatuses, to generate a universal triggering signal for the one or more components on the basis of said received triggering signal from the selected triggering apparatus, and to send the universal triggering signal to the one or more components.

17 Claims, 5 Drawing Sheets

DEVICE FOR SELECTING A BEAM TRIGGERING APPARATUS

CROSS REFERENCE TO RELATED APPLICATIONS

This application is a national phase application of International Application No. PCT/EP2009/054529, filed Apr. 16, 2009, designating the United States and claiming priority to European Patent Application No. 08154632.7, filed Apr. 16, 2008, both of which are incorporated by reference herein in their entirety.

FIELD OF THE INVENTION

The present invention is related to a system and method for radiation therapy. In particular, the invention is related to physiological gating of radiation therapy.

STATE OF THE ART

In radiotherapy procedures such as particle radiation therapy, it is important to deliver a high dose to a target volume while minimizing the dose to surrounding healthy tissues. A particle radiation therapy apparatus comprises various components such as a beam delivery system, a patient positioning system and a patient positioning verification system. The beam delivery system comprises a particle accelerator for producing energetic particle beams, a beam transport system to bring the particle beam to a treatment room and a nozzle for shaping the beam. The nozzle is responsible for delivering a conformal dose distribution to the target volume and for monitoring and measuring the delivered dose.

Due to physiological movements of the patient, for example the patient's respiratory movements or heart movement, the target volume can move during irradiation which can result in insufficient dose delivery to the target volume and more dose delivery to surrounding healthy tissues. To solve this problem the radiation beam is subjected to a gating technique, wherein the beam may be interrupted at given points in time, and triggered again when the position of the patient returns to a given state. Detection of the patient's movements may be done by various techniques (e.g. monitoring the position of external body markers, monitoring the air volume in the lungs, breath holding method, monitoring fiducials inside the patient's body, . . . ). This information can then be used for commanding a beam gating scheme.

Today, various apparatuses have become commercially available on the market to track the respiratory cycle of a patient. These devices are using various techniques: devices based on optical tracking of marker displacements (e.g. the Real-time Position Management system (RPM) by Varian Medical Systems), devices based on the measurement of the patient's air flow (e.g. spirometer based systems provided by Dyn'R or the Active Breathing Control system from Elekta), systems based on fluoroscopy, etc. In radiation treatment facilities, various techniques to monitor physiological motions and various triggering apparatuses are used for specific types of treatments and patients. Each of the physiological cycle measuring devices has its advantages and disadvantages and the physician selects the more appropriate system according to the tumour type (lung, prostate, . . . ). The use of different triggering apparatuses causes problems with respect to installation and with respect to safety. For each type of triggering apparatus, equipment needs to be re-installed in the treatment room and in the treatment control room, cables need to be disconnected and reconnected and possibly a re-configuration of the control desk's command tools needs to be made. These operations represent an error risk. After each re-installation a quality control needs to be performed to guarantee proper operation of the beam gating system.

In addition, in particle radiation therapy, prior to the beam irradiation, the position of the target volume is verified using a patient positioning verification system. An example of such a system is an orthogonal X-ray system. With such a system X-ray radiographs are taken and compared with a set of reference radiographs and corrections can be made to the patient's position. Such a positioning verification system can also be sensitive to physiological motions of the patient. For example if fiducials have been implanted in the patient and used as reference points, the position of the fiducials can change with the breathing cycle of the patient. To solve this problem, the position verification system can be enabled/disabled following a triggering signal from a physiological cycle measuring device. In a radiation treatment facility, not only various types of triggering apparatus can be made available, also various types of positioning verification systems (X-ray based systems, infra-red camera, . . . ) can be used according to a specific treatment. The use of a physiological cycle measuring device for the purpose of patient positioning verification and for the purpose of particle beam delivery causes an additional problem with respect to (re)installation and safety as cables need to be disconnected and reconnected.

When performing patient treatment sessions, the switching of various types of physiological cycle measuring devices and the use of the resulting gating signal on the one hand for patient positioning verification and on the other hand for gating a beam delivery system, not only causes risks with respect to safety as discussed above but also the overall treatment session time is increased resulting in a reduction of patient throughput.

Document WO99/42034 discloses a device for coordinating a medical treatment with a respiratory cycle of a patient who is breathing with the help of a ventilator. The device may comprise a rotatable knob which allows the operator to choose between a number of existing ventilator models. However, the device still suffers from the described drawbacks, as the selection of a type of ventilator requires disconnecting a ventilator and re-connecting to the selected ventilator type.

AIMS OF THE INVENTION

The present invention aims to solve the above described problems. In particular, the invention aims to provide a more reliable change between triggering apparatuses and/or between components of a radiation treatment apparatus installed in connection with a radiation treatment room.

SUMMARY OF THE INVENTION

The present invention is related to a device for selecting one of several triggering apparatuses, which are simultaneously connectable to said device, said triggering apparatuses being arranged for producing each a triggering signal to enable/disable one or more components of a radiation treatment apparatus, said triggering signals depending on detected parameters, the device comprising:
  means for receiving triggering signals from said several triggering apparatuses, when all of said apparatuses are connected to the device,
  input means for selecting one of said triggering apparatuses, means for generating a universal triggering signal for said one or more components on the basis of said received triggering signal from said selected triggering apparatus, means for sending the universal triggering signal to said one or more components.

Said input means for selecting one of said triggering apparatuses (3-6) may comprise a control panel having a switch (20) to manually select the triggering apparatus.

Said switch may be a turnable knob (20), arranged to select one of said triggering apparatuses (3-6), or a manual triggering method, or a state wherein no triggering of the beam is performed.

The device of the invention may comprise means to select a manual triggering method, and a switch to manually enable/disable a component.

Said input means for selecting one of said triggering apparatuses may comprise means for receiving the selection of the triggering apparatus from an external system and for automatically selecting the triggering apparatus according to the received selection.

Said input means, said means for generating and said means for sending may be adapted for selecting, generating and sending a permanently enabled triggering signal.

The device of the invention may further comprise selection means for selecting a component from said one or more components.

Said selection means for selecting a component may comprise a control panel having a switch to select the component. Said selection means for selecting a component from said one or more components may comprise means for receiving from an external system the selection of the component and for automatically selecting the component according to the received selection.

The device of the invention may further comprise:
means for sending signals to the said several triggering apparatuses
means for receiving signals from said one or more components.

According to an embodiment, the device of the invention comprises for each triggering apparatus connectable to the device, a pair of switches being arranged in series, the first of said pair of switches being arranged to close when the corresponding triggering apparatus is selected, the second of said pair of switches being arranged to close or open in accordance with a triggering signal received from the corresponding triggering apparatus, the device further being arranged so that said universal triggering signal is generated when both switches are closed.

The invention is equally related to a method for treating a patient by using a device according to the invention, said device being coupled to two or more beam triggering devices (3-6) and to a radiation treatment apparatus, said apparatus comprising a beam delivery system and possibly other components, the method comprising the steps of:
selecting one of said triggering apparatuses connected to the UBTI device;
receiving a triggering signal (230) from the selected triggering apparatus;
generating a gating signal for enabling/disabling said beam delivery system in accordance with said triggering signal;
irradiating said patient with said beam delivery system in accordance with said gating signal.

Said radiation treatment apparatus may comprise several beam delivery systems, in which the method comprises the steps of:

selecting one of said triggering apparatuses connected to the UBTI device;
receiving a triggering signal from the selected triggering apparatus;
selecting a beam delivery system,
generating a gating signal for enabling/disabling said beam delivery system in accordance with said triggering signal;
irradiating said patient with said beam delivery system in accordance with said gating signal.

According to an embodiment, said radiation treatment apparatus further comprises a patient positioning verification system and said steps are preceded by the steps of:
selecting one of said triggering apparatuses connected to the UBTI device;
selecting said patient positioning verification system,
receiving a triggering signal from the selected triggering apparatus;
generating a gating signal for enabling/disabling said patient positioning verification system;
performing said patient positioning verification in accordance with said gating signal.

According to an embodiment, said radiation treatment apparatus further comprises a patient positioning verification system and said steps and the steps of irradiating said patient and of performing said patient positioning verification are performed simultaneously.

BRIEF DESCRIPTION OF THE FIGURES

FIG. 3b shows the back panel of the exemplary device of FIG. 3a.

DETAILED DESCRIPTION OF THE INVENTION

Figure 1:
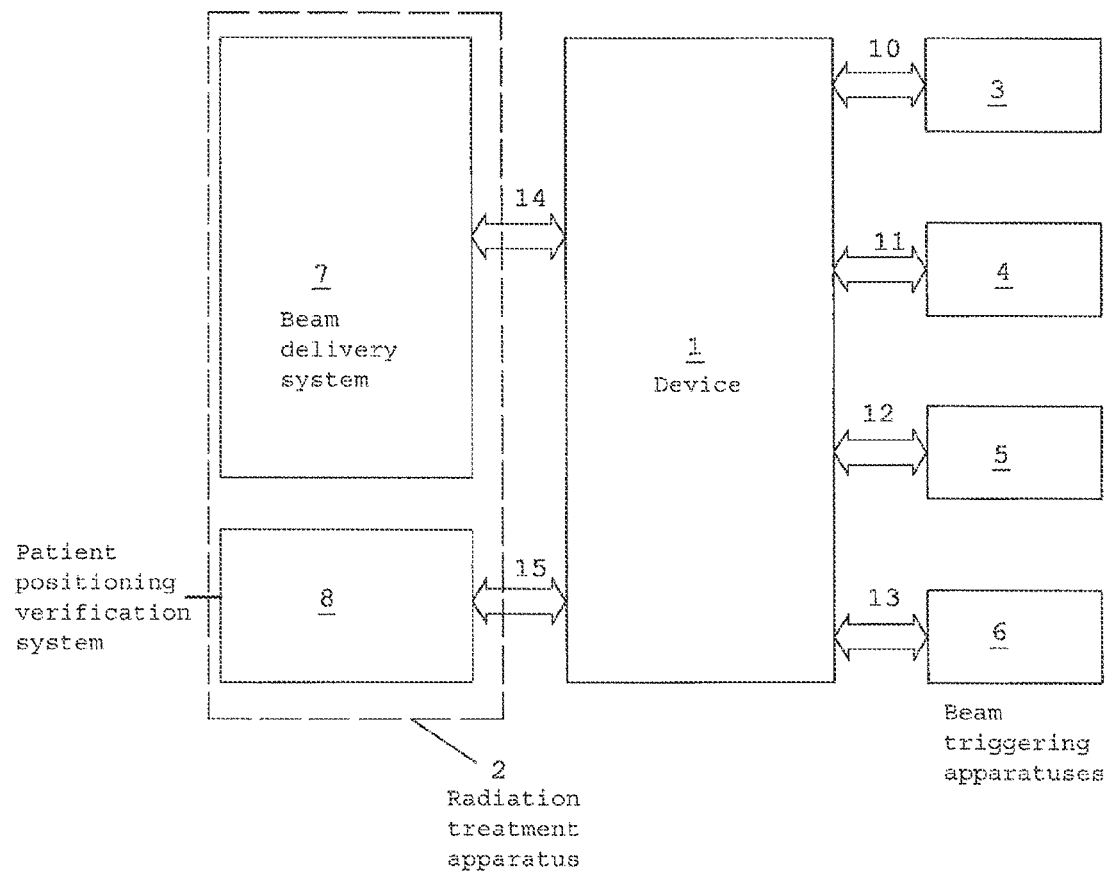
FIG. 1 illustrates schematically how the apparatus of the invention is connected to a number of triggering apparatuses and to one or more components of a radiation treatment apparatus (e.g. a beam delivery system or a patient positioning verification system).

One or more embodiments of the present invention will now be described in detail with reference to the attached figures, the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention. Those skilled in the art can recognize numerous variations and modifications of this invention that are encompassed by its scope. Accordingly, the description of preferred embodiments should not be deemed to limit the scope of the present invention.

Figure 2:
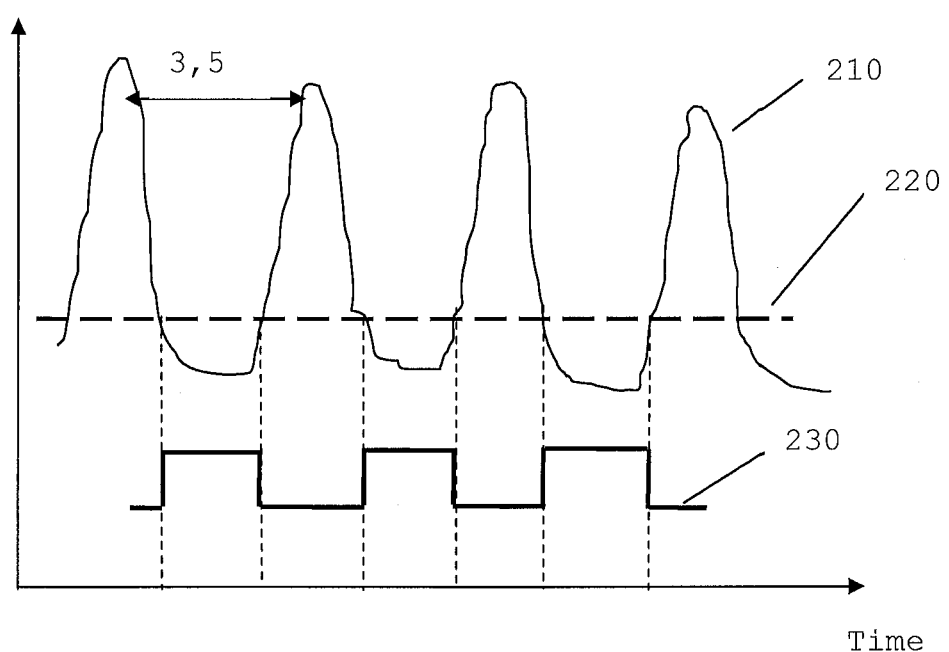
FIG. 2 illustrates schematically a physiological cycle and a gating signal resulting from a selection of a phase of the cycle by defining a threshold.

With reference to FIG. 1, the device 1 of the invention is a device which is connected between a radiation treatment apparatus 2 and a number of beam triggering apparatuses 3 to 6. A 'beam triggering apparatus' in the context of this invention, is defined as the totality of equipment used in the treatment room to produce a triggering signal based on detected parameters, allowing to measure a physiological cycle of a patient (e.g. a device to measure breathing volume, a camera to monitor the position of external markers on the patient, cables, . . . ). Controller means are further required (basically a computer), for receiving the detected signals, calculating a gating interval on the basis of these signals, and sending out command signals to turn the beam on or off, i.e. sending out the gating control signal. The gating control signal carries timing information relating to the start and stop of a predetermined phase of said physiological cycle. The beam triggering apparatuses are also named physiological cycle measuring devices or "PCMD" and the gating control signal provided by a PCMD can be named PCMD gating signal. An example of a PCMD is a respiratory cycle measuring device. Various types of respiratory cycle measuring devices are available on the market. For example the Real Time Position Management (RPM) respiratory gating system from Varian Medical Systems is using an infrared tracking camera and a reflective marker for measuring the patient's respiratory pattern. Thresholds are set when the respiratory cycle is in a selected phase of the cycle. The respiratory gating system provides a gating control signal corresponding to the selected phase of a respiratory cycle. This basic principle of using a PCMD is schematically illustrated in FIG. 2 where signal 210 is representing a respiratory cycle and by defining a threshold 220, a PCMD gating signal 230 is generated. This is the 'triggering signal' produced by the triggering apparatus. This PCMD gating signal 230 can then be used to enable or disable a device or component of a radiation treatment apparatus. The PCMD gating signal 230 can be a periodic square wave or box-type signal as illustrated in FIG. 2.

The radiation treatment apparatus 2 may comprise various components. It comprises a beam delivery system 7 (BDS), and possibly further components such as a patient positioning system (not shown on FIG. 1) and a patient positioning verification system 8 (PPVS). The beam delivery system 7 is a schematic representation of the radiation beam source and its control and display equipment (e.g. a particle therapy beam delivery system, an IMRT beam delivery system, . . . ). The beam delivery system 7 may comprise a particle accelerator for producing energetic particle beams, a beam transport system to bring the particle beam to a treatment room, a nozzle for shaping the beam and a control system. The radiation treatment apparatus 2 can comprise multiple nozzles which can be installed in multiple treatment rooms, or multiple nozzles could be installed in the same treatment room. The beam delivery system 7 or components of the beam delivery system can be connected to the device of the invention 1. The control equipment of the beam delivery system comprises the means to control the hardware equipment, means to monitor the beam delivery, means to turn the beam on or off and means to display different parameters of the irradiation process.

In addition, a patient positioning verification system 8 can also be connected to the device of invention 1. This patient positioning verification system 8 is for example an imaging system based on orthogonal X-rays but it can also be another device which is used for the purpose of verifying the patient's position (e.g. volumetric imaging device, . . . ).

A treatment room is defined as a room wherein one patient may receive particle therapy. Such a room comprises a nozzle, a patient positioning system, various patient positioning verification systems, various triggering apparatuses and other equipment.

The apparatus of the invention 1 is hereafter called 'universal beam triggering interface' or UBTI. The UBTI 1 is an electronic device having at least two interfaces 10-13 for connecting the device to two or more different beam triggering apparatuses, e.g. an RPM triggering device and a spirometer based triggering device, installed in the same treatment room, and which can all be simultaneously connected to the UBTI. The UBTI has one interface 14 to the radiation beam delivery system 7 and one or more interfaces (15) to one or more patient positioning verification systems such as the X-ray system 8, or to other components such as a volumetric imaging device. Interfaces 10-13 may be bi-directional, as shown, or they may be uni-directional, wherein there is communication only from the beam triggering apparatus (3-6) to the UBTI 1. Likewise, interfaces 14-15 may be bi-directional, as shown, or they may be uni-directional wherein there is communication only from the UBTI to the components 7-8.

Figure 3A:
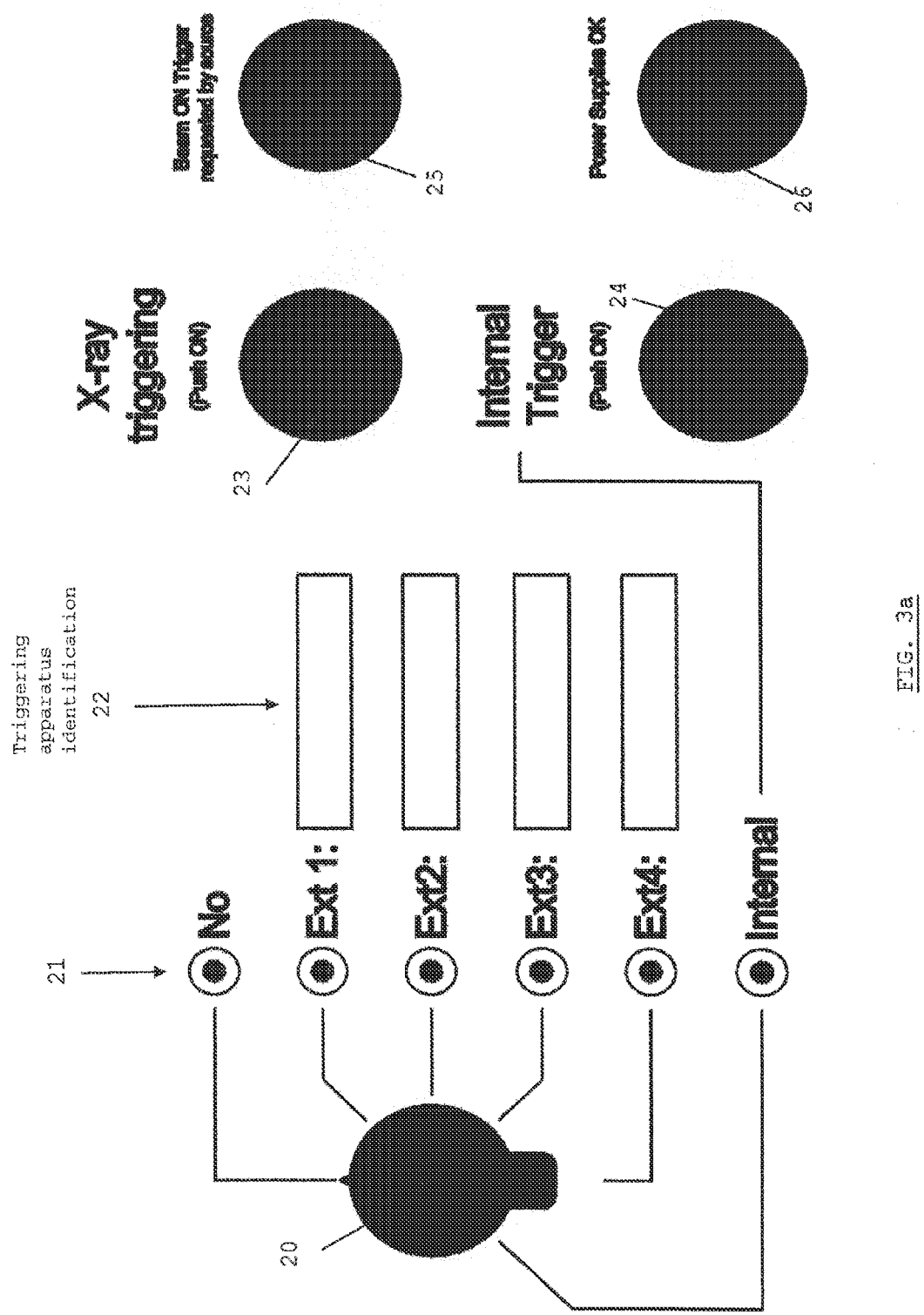
FIG. 3a illustrates a possible view of the control panel of a device of the invention.

The UBTI further comprises an input means, preferably in the form of a control panel, which may look like the example shown in FIG. 3a. This control panel has a rotating knob 20, which can be turned to select a total of six positions, indicated by the LED's 21. LEDs marked 'Ext1' to 'Ext4' indicate 4 particular external beam triggering apparatuses, installed in the treatment room. In the rectangles 22 next to the LEDs, the triggering apparatus is identified (e.g. Dyn'R, RPM, etc. . . . ). The top LED ('No') corresponds to the status wherein no beam triggering/gating is done. This corresponds to the case where the input means, means for generating signals and means for sending signals in the device of the invention are adapted for selecting, generating and sending a permanently enabled triggering signal. The bottom LED ('Internal') corresponds to the status wherein an internal, i.e. manual triggering is done. Manual triggering can for example be applied based on fluoroscopy images acquired in real time during the treatment.

In the embodiment shown in FIG. 3a, the radiation beam apparatus is equipped with one patient positioning verification system 8 based on orthogonal X-rays. A first switch (button 23) is present to activate (i.e. select) component 8, i.e. the triggering/gating of the orthogonal X-ray system used for verifying or correcting the patient's position. Pressing the button 23 means that X-rays can only be taken in accordance with the triggering signal defined by the selected triggering apparatus. It must be noted that the sending of a gating signal to a component, e.g. a beam delivery system, does normally not activate the component automatically. In most cases, further synchronisation is needed between a timing signal generated by the beam delivery system and the gating signal. This timing signal can for example be a clock signal having a frequency corresponding to the rotation of a range modulator wheel (e.g. 10 Hz signal) or it may be determined by the frequency of a synchrotron pulse. This synchronisation can take place according to any known method. The actual beam delivery is therefore activated separately from the UBTI, whereas the UBTI provides the gating signal which is to be applied to the beam delivery. For this reason, it may be also be possible, as is the case with the interface of FIG. 3a (see further for the internal circuitry) to deliver the gating signal to both the beam delivery system and to an X-ray system, without necessarily activating both systems simultaneously.

Another switch (button 24) is present, for activating the manual trigger of the selected component. This button switch is preferably produced in such a way that the user must keep the button pressed down to keep the component enabled. As soon as the user releases the button, the component is disabled. This function is only possible when the knob 20 points to the bottom LED ('internal').

Two larger LEDS are present. The first one indicates that a beam ON trigger is produced by the selected triggering apparatus. This is an indicator which visualises the triggering signals, e.g. by blinking on/off following the input triggering signal from the selected triggering apparatus. The second one 26 indicates that the power of the device is on.

The UBTI is provided with a means for generating a universal triggering signal (further also called (UBTI) gating signal) for the selected component. For example in the case of FIG. 1, the UBTI is provided with means for generating a UBTI gating signal for a component 7, 8 of radiation treatment apparatus 2 (e.g. beam delivery system 7, patient positioning verification system 8) to control the enabling and disabling of the component 7, 8. Gating signals to be generated for a beam delivery system or for a patient positioning verification system can be different. In the preferred embodiment of the invention, the UBTI is equipped with electronics to generate UBTI gating signals for both a beam delivery system for particle therapy 7 and a patient positioning verification system 8.

The UBTI gating signal is based on the triggering signal (gating control signal) received from the selected triggering apparatus. This means that the gating signal is generated in synchronicity with the gating control signal. The UBTI gating signal preferably follows the gating control signal with a minimum delay. Signal characteristics (signal level, etc.) of the UBTI gating signal for a given component are preferably independent of the triggering apparatus which is selected. When a particular beam triggering apparatus is selected by turning the knob 20 on the control panel of the UBTI into the corresponding position, the selected triggering apparatus (after it has been made operational e.g. by connecting sensors to the patient's body), will transmit a triggering signal (gating control signal) to the UBTI, and the UBTI will generate and send a UBTI gating signal to the beam delivery system. When the button 23 is activated, the UBTI will generate and send a UBTI gating signal to the orthogonal X-ray system. When the interfaces 10-15 are bidirectional, the UBTI may be provided with means for receiving signals from a selected component and means for sending signals to the selected triggering apparatus. In this embodiment, the UBTI may be equipped with added functionality, such as a means for controlling (e.g. delaying a gating signal, adjusting a gating interval) a selected triggering apparatus.

According to an embodiment, a number of components of the radiation treatment apparatus 2 may be selected and activated simultaneously. For example, the UBTI device may be arranged to allow simultaneous patient positioning verification by X-rays and beam treatment, both the X-ray verification and beam treatment being applied according to the triggering signal produced by the selected triggering apparatus.

Figure 3B:
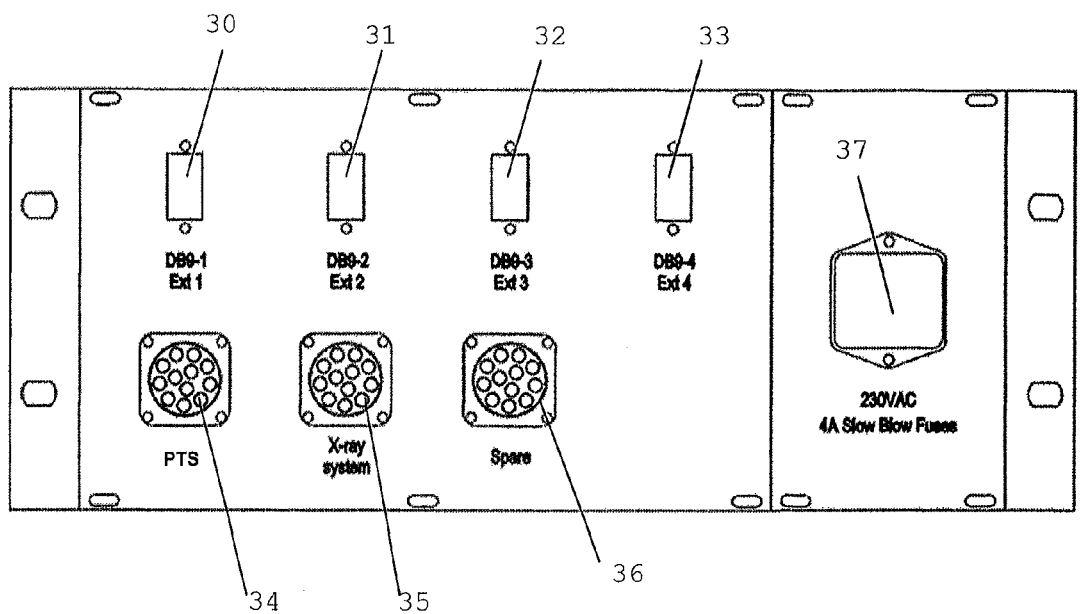

In the embodiment shown in FIGS. 3a-3b, up to four different beam triggering apparatuses may be connected to the UBTI at the same time. The control panel allows the operator to select the beam triggering apparatus, simply by turning the knob. No cables need to be disconnected/re-connected. The device of the invention is not limited to the version shown, and can be adapted to select between any number N (N≥1) of triggering apparatuses and various other components.

FIG. 3b shows a view of the back panel of the UBTI of FIG. 3a. Four inputs (multiwire connectors 30-33) are visible for connection to four triggering apparatuses. Three outputs (multiwire connectors 34-36) are visible for connection to a PTS (Particle Treatment System), i.e. a beam delivery system, an X-ray system (Patient positioning verification), a 'spare' outlet, for example for another patient positioning verification system. An input for 220 VAC power supply is denoted by reference 37.

Figure 4:
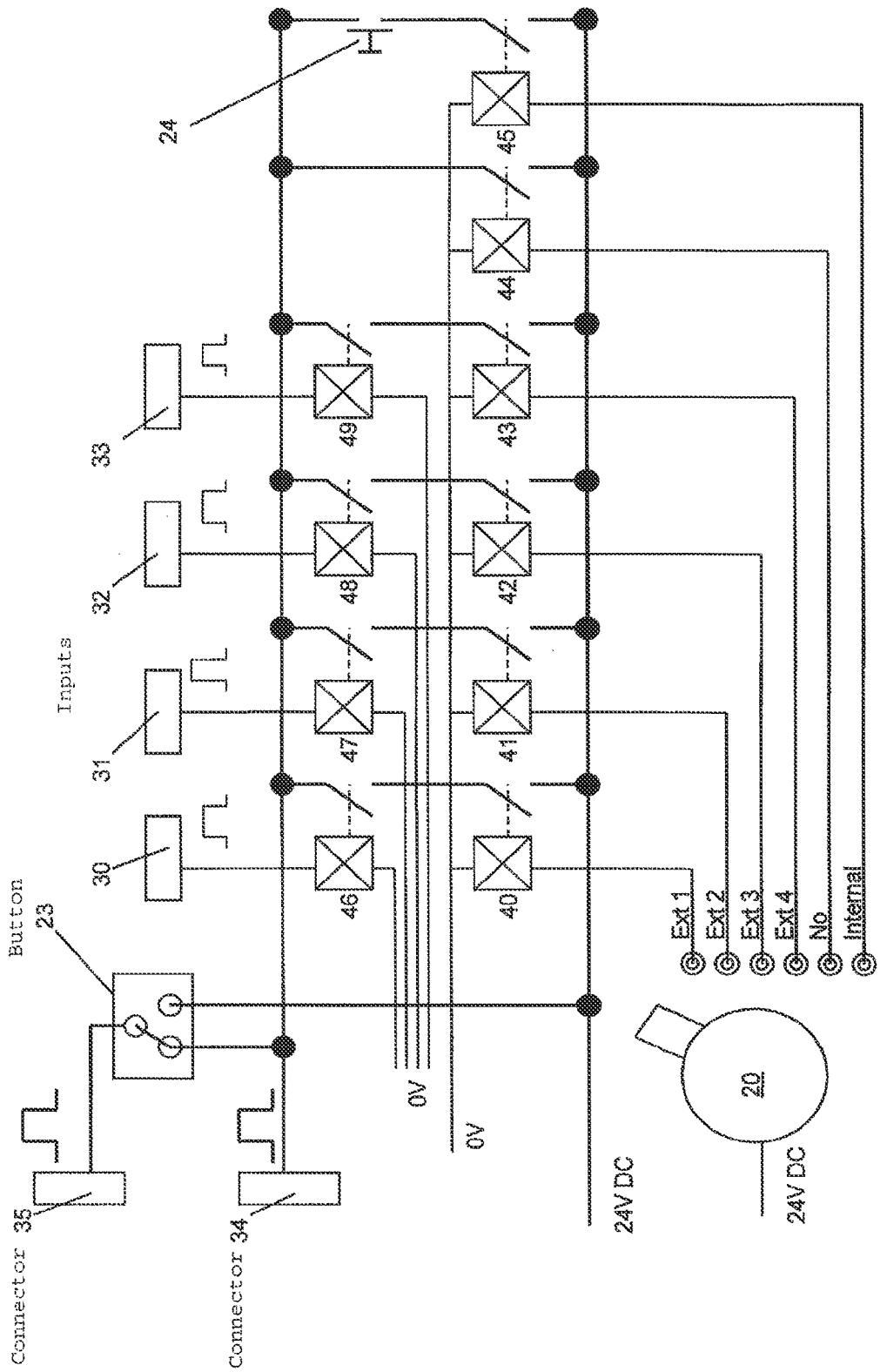
FIG. 4 gives a schematic view of the main internal operating components in a preferred embodiment of a device according to the invention.

FIG. 4 shows a schematic of the internal operation of the UBTI, according to a preferred embodiment. The image shows the four inputs 30-33, and the outputs 34 (labelled 'PTS') and 35 (labelled 'X ray system') on the back panel. Relay-operated switches 40-45 are arranged so that one of these switches closes when the rotatable knob 20 is turned to select one of the six available options, i.e. four triggering apparatuses, connected to the UBTI, the 'no' option (no triggering) and the 'internal' option (manual triggering). Four more switches 46-49 are commanded by the gating control signal produced by the four triggering apparatuses. For each of the four apparatuses, the knob-operated switch is arranged in series with the trigger-operated switch, and these four series-arrangements are themselves arranged in parallel, and connected to the output 34, in such a way that only the simultaneous closing of e.g. switches 40 and 46 allows the beam to be triggered by the triggering apparatus connected to input 30. Selection of the 'no' and 'internal' options leads to closing of the switches 44 and 45 respectively. The switch is arranged in parallel to the series-arrangements referred to above, so that selection of the 'no' option automatically leads to a permanent (i.e. not gated) enablement of the beam. The switch 45 is arranged in series with the button-operated switch 24, thereby only allowing beam operation when button 24 is pressed down. The switches 46-49 must close fast in order for the gating signal to follow the gating control signals with a minimum delay. Preferably, these switches are operated by fast relays having a reaction time of 5 ms or less. The operating voltage of the relays 40-45 may be 24V. The operating voltage of fast relays 46-49 depends on the triggering apparatuses connected to the UBTI, and may differ between different types of such apparatus (e.g. 12 or 24V).

The operation of button 23 of FIG. 3a is also illustrated on FIG. 4. Activating the button (left position of the switch) will send the same gating signal to connectors 34 and 35, thereby allowing both the X-ray apparatus and the beam to be triggered by the same signal. De-activating the button 23 (right position of the switch) means that the X-ray is permanently enabled. This means that it can be activated, but it cannot be triggered by a triggering signal (i.e. this is analogue to the 'no' option for the beam delivery system).

The system of FIGS. 3a and 4 is an example where the same gating signal can be sent to both a beam delivery system and a patient positioning verification system, which would allow also a simultaneous gated activation of both these components, i.e. patient positioning verification during beam irradiation.

According to another embodiment (not shown in the drawings), the control panel comprises an additional rotatable knob or similar means, which allows the user to actively select a component of the radiation treatment apparatus 2. A selection can for example be made between different types of patient position verification systems available in the treatment room (e.g. X-ray, infrared camera, . . . ). A selection may further be possible between multiple nozzles if multiple nozzles are available in the same treatment room (which can be seen as a selection between multiple beam delivery systems, even if the nozzles are connected to the same radiation source).

Preferably, the power supply towards the triggering apparatuses is provided through input connectors 30-33, by connecting two pins on the input connectors to a reference and supply voltage respectively. Separate voltage supply devices may be incorporated in the UBTI for each of the triggering apparatuses, or a single voltage supply may be internally transformed to the appropriate supply voltage for each triggering apparatus.

Circuiting within the UBTI may be arranged such that through the multi-wire connectors 30-33, the UBTI can receive e.g. health status information from the triggering apparatus and/or status information (e.g. selected triggering device) can be sent from the UBTI to the PTS through multi-wire connector 34.

According to an embodiment, the input means for selecting one of said triggering apparatuses and/or components comprises means for receiving the selection of the triggering apparatus and/or component from an external system and for automatically selecting the triggering apparatus and/or component according to the received selection. An example of an external system from which the UBTI can receive trigger selection information is the control system of the PTS or in another example the UBTI could receive direct trigger selection information from a so-called Oncology Information System (OIS). In this embodiment, the rotatable knob(s) may be absent, and an interface is provided for connecting the external system to the UBTI and for receiving the appropriate command signals from said external system.

The invention is equally related to a method for treating a patient by using a UBTI device according to the invention, said device being coupled to two or more beam triggering devices (3-6) and to a radiation treatment apparatus 2, said apparatus comprising a beam delivery system and possibly other components, the method comprising the steps of:

selecting one of said triggering apparatuses connected to the UBTI device;
receiving a triggering signal from the selected triggering apparatus;
generating a gating signal for enabling/disabling said beam delivery system in accordance with said triggering signal;
irradiating said patient with said beam delivery system in accordance with said gating signal.

According to an embodiment, the radiation treatment apparatus may comprise several beam delivery systems (e.g. several nozzles installed in the same treatment room). In this case, the method comprises the steps of:

selecting one of said triggering apparatuses connected to the UBTI device;
receiving a triggering signal from the selected triggering apparatus;
selecting a beam delivery system,
generating a gating signal for enabling/disabling said beam delivery system in accordance with said triggering signal;
irradiating said patient with said beam delivery system in accordance with said gating signal.

Preferably, one of said components is a patient positioning verification system 8, and the above steps are preceded by the following steps:

selecting one of said triggering apparatuses connected to the UBTI device;
selecting said patient positioning verification system,
receiving a triggering signal from the selected triggering apparatus;
generating a gating signal for enabling/disabling said patient positioning verification system;
performing said patient positioning verification in accordance with said gating signal.

Alternatively, both a beam delivery system and patient positioning system may be selected at the same time, and the steps of irradiating and performing patient positioning verification may be done simultaneously. Also, when more components of the radiation treatment apparatus are available and connected to the UBTI device, the method may comprise steps of selecting said components and activating said components in accordance with a UBTI gating signal generated in accordance with a triggering signal produced by the selected triggering apparatus.

The invention claimed is:

1. A device for selecting one of several triggering apparatuses which are simultaneously connectable to said device, said triggering apparatuses being arranged for producing each a triggering signal to enable/disable one or more components of a radiation treatment apparatus, said triggering signals depending on detected parameters, the device comprising:
   means for receiving triggering signals from said several triggering apparatuses, when all of said apparatuses are connected to the device,
   input means for selecting one of said triggering apparatuses,
   means for generating a universal triggering signal for said one or more components on the basis of said received triggering signal from said selected triggering apparatus,
   means for sending the universal triggering signal to said one or more components.

2. The device according to claim 1, wherein said input means for selecting one of said triggering apparatuses comprises a control panel having a switch to manually select the triggering apparatus.

3. The device according to claim 2, wherein said switch is a turnable knob, arranged to select one of said triggering apparatuses or a manual triggering method, or a state wherein no triggering of the beam is performed.

4. The device according to claim 1, wherein the device comprises means to select a manual triggering method, and a switch to manually enable/disable a component.

5. The device according to claim 1, wherein said input means for selecting one of said triggering apparatuses comprises means for receiving the selection of the triggering apparatus from an external system and for automatically selecting the triggering apparatus according to the received selection.

6. The device according to claim 1, wherein said input means, said means for generating and said means for sending are adapted for selecting, generating and sending a permanently enabled triggering signal.

7. The device according to any claim 1, wherein the device further comprises selection means for selecting a component from said one or more components.

8. The device according to claim 7, wherein said selection means for selecting a component comprises a control panel having a switch to select the component.

9. The device according to claim 7, wherein said selection means for selecting a component from said one or more components comprises means for receiving from an external system the selection of the component and for automatically selecting the component according to the received selection.

10. The device according to claim 1, the device further comprising:
    means for sending signals to the said several triggering apparatuses
    means for receiving signals from said one or more components.

11. The device according to claim 1, comprising for each triggering apparatus connectable to the device, a pair of switches being arranged in series, the first of said pair of switches being arranged to close when the corresponding triggering apparatus is selected, the second of said pair of switches being arranged to close or open in accordance with a triggering signal received from the corresponding triggering apparatus, the device further being arranged so that said universal triggering signal is generated when both switches are closed.

12. A method for treating a patient by using a device according to claim 1, said apparatus comprising a beam delivery system, the method comprising the steps of:
- selecting one of said triggering apparatuses connected to the device;
- receiving a triggering signal from the selected triggering apparatus;
- generating a gating signal for enabling/disabling said beam delivery system in accordance with said triggering signal; and
- irradiating said patient with said beam delivery system in accordance with said gating signal.

13. The method according to claim 12, wherein said radiation treatment apparatus comprises several beam delivery systems, and wherein the method comprises the steps of:
- selecting one of said triggering apparatuses connected to the device;
- receiving a triggering signal from the selected triggering apparatus;
- selecting a beam delivery system;
- generating a gating signal for enabling/disabling said beam delivery system in accordance with said triggering signal; and
- irradiating said patient with said beam delivery system in accordance with said gating signal.

14. The method according to claim 12, wherein said radiation treatment apparatus further comprises a patient positioning verification system and wherein said steps are preceded by the steps of:
- selecting one of said triggering apparatuses connected to the device;
- selecting said patient positioning verification system;
- receiving a triggering signal from the selected triggering apparatus;
- generating a gating signal for enabling/disabling said patient positioning verification system; and
- performing said patient positioning verification in accordance with said gating signal.

15. The method according to claim 12, wherein said radiation treatment apparatus further comprises a patient positioning verification system and wherein said steps and the steps of irradiating said patient and of performing said patient positioning verification are performed simultaneously.

16. A device for selecting one of a plurality of triggering apparatuses which are simultaneously connected to the device, the triggering apparatuses configured to produce triggering signals to enable/disable one or more components of a radiation treatment apparatus, the triggering signals depending on detected parameters, the device comprising:
- a controller which receives the triggering signals from the plurality of triggering apparatuses,
- an input device which receives an input for selecting one of the plurality of triggering apparatuses,
- a generating device which generates a universal triggering signal for the one or more components on the basis of the received triggering signal from the selected triggering apparatus, and
- an output device which sends the universal triggering signal to the one or more components.

17. A method for treating a patient by using a device, the device being coupled to two or more beam triggering apparatuses and to a radiation treatment apparatus comprising a beam delivery system, the method comprising the steps of:
- selecting one of the two or more triggering apparatuses connected to the device;
- receiving a triggering signal from the selected triggering apparatus;
- generating a signal for enabling/disabling the beam delivery system in response to receiving the triggering signal; and
- irradiating a patient with the beam delivery system in accordance with said gating signal.

* * * * *